(12) United States Patent
Zeller et al.

(10) Patent No.: US 8,147,560 B2
(45) Date of Patent: Apr. 3, 2012

(54) IMPLANT AND METHOD FOR THE PRODUCTION OF AN IMPLANT

(75) Inventors: Richard Zeller, Tuttlingen (DE); Jan Reich, Tuningen (DE); Fred-Rainer Grohmann, Urdorf (CH)

(73) Assignees: Ionbond AG Olten, Olten (CH); Aesculap AG, Tuttlingen (DE)

( * ) Notice: Subject to any disclaimer, the term of this patent is extended or adjusted under 35 U.S.C. 154(b) by 401 days.

(21) Appl. No.: 12/322,511

(22) Filed: Feb. 2, 2009

(65) Prior Publication Data

US 2009/0210068 A1 Aug. 20, 2009

Related U.S. Application Data

(63) Continuation of application No. PCT/EP2007/057502, filed on Jul. 20, 2007.

(30) Foreign Application Priority Data

Aug. 16, 2006 (DE) .......................... 10 2006 039 329

(51) Int. Cl.
*A61F 2/28* (2006.01)
(52) U.S. Cl. ................ 623/23.56; 623/23.36; 623/23.53
(58) Field of Classification Search ............... 623/23.36, 623/23.53, 23.56
See application file for complete search history.

(56) References Cited

U.S. PATENT DOCUMENTS

| | | | |
|---|---|---|---|
| 5,415,704 A | 5/1995 | Davidson | |
| 5,498,302 A | 3/1996 | Davidson | |
| 5,820,941 A | 10/1998 | Felton et al. | |
| 6,224,968 B1 | 5/2001 | Van Den Berg | |
| 6,617,057 B2 | 9/2003 | Gorokhovsky et al. | |
| 7,150,818 B2 | 12/2006 | Christensen et al. | |
| 7,156,851 B2 | 1/2007 | Christensen et al. | |
| 7,520,947 B2 | 4/2009 | Kennedy et al. | |
| 2003/0010929 A1 | 1/2003 | Priewe et al. | |
| 2004/0068323 A1 | 4/2004 | Christensen | |

(Continued)

FOREIGN PATENT DOCUMENTS

DE 250 462 10/1987

(Continued)

OTHER PUBLICATIONS

"Material: Aluminum Oxide", http://www.memsnet.org/material/aluminumoxideal2o3bulk/, accessed Oct. 5, 2011.*

*Primary Examiner* — Thomas J Sweet
*Assistant Examiner* — Megan Wolf
(74) *Attorney, Agent, or Firm* — Lipsitz & McAllister, LLC

(57) ABSTRACT

An implant for insertion into a human or animal body which comprises at least one implant part is provided. The at least one implant part has a base member which is produced from an implant material and has a surface which is designed at least partially in the form of an artificial joint surface. Part of or the entire joint surface is covered with a wear-reducing hard material coating, such that a service life of the implant is extended and the compatibility of the implant increased. An intermediate layer is provided between the hard material coating and the at least one joint surface formed from the implant material for the purpose of reducing tension between the hard material coating and the implant material. A corresponding method for production of an implant is also provided.

29 Claims, 4 Drawing Sheets

U.S. PATENT DOCUMENTS

| | | |
|---|---|---|
| 2004/0236433 A1 | 11/2004 | Kennedy et al. |
| 2005/0258047 A1 | 11/2005 | Christensen et al. |
| 2007/0078521 A1* | 4/2007 | Overholser et al. ........ 623/23.53 |

FOREIGN PATENT DOCUMENTS

| | | |
|---|---|---|
| DE | 37 28 836 | 3/1988 |
| DE | 40 12 048 | 10/1991 |
| DE | 296 17 507 | 3/1998 |
| DE | 694 14 872 | 4/1999 |
| DE | 693 25 042 | 11/1999 |
| DE | 100 04 832 | 8/2001 |
| DE | 20 2005 005 405 | 6/2005 |
| DE | 602 00 884 | 8/2005 |
| EP | 0 248 117 | 12/1987 |
| EP | 1 679 088 | 7/2006 |
| GB | 2 195 664 | 4/1988 |
| WO | 2005007909 | 1/2005 |
| WO | 2006/069465 | 6/2006 |

* cited by examiner

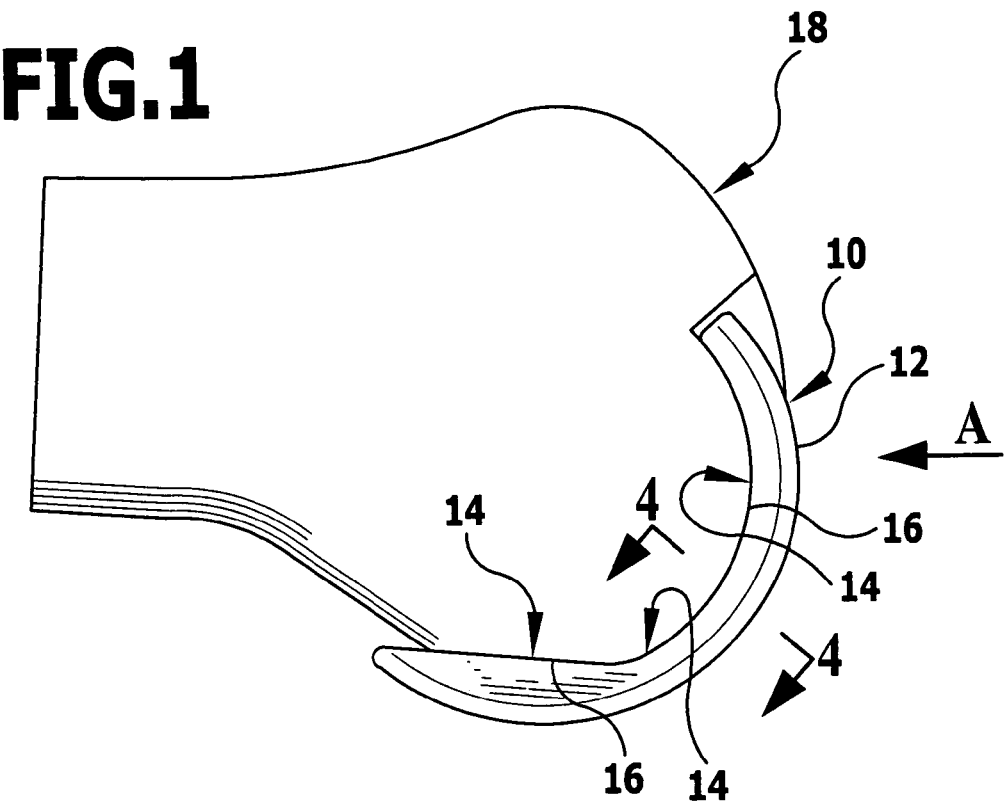
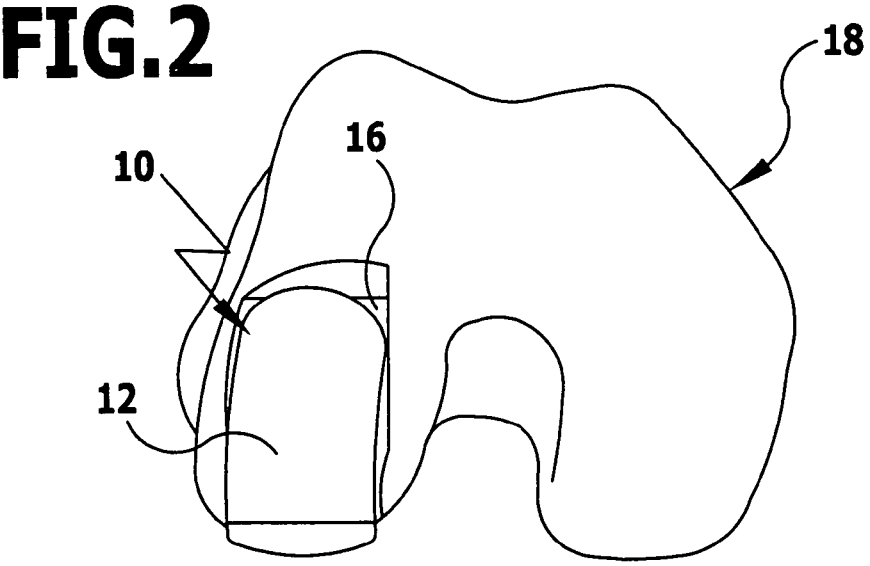

IMPLANT AND METHOD FOR THE PRODUCTION OF AN IMPLANT

CROSS-REFERENCE TO RELATED APPLICATIONS

This application is a continuation of International application No. PCT/EP2007/057502 filed on Jul. 20, 2007.

The present disclosure relates to the subject matter disclosed in International application No. PCT/EP2007/057502 of Jul. 20, 2007 and German application No. 10 2006 039 329.5 of Aug. 16, 2006, which are incorporated herein by reference in their entirety and for all purposes.

FIELD OF THE INVENTION

The present invention relates to an implant for insertion into a human or animal body generally, and more specifically to an implant for insertion into a human or animal body which comprises at least one implant part, wherein the at least one implant part has a base member which is produced from an implant material and has a surface which is designed at least partially in the form of an artificial joint surface, wherein part of or the entire joint surface is covered by a wear-reducing hard material coating.

BACKGROUND OF THE INVENTION

Furthermore, the present invention relates to a method for the production of an implant for insertion into a human or animal body which comprises at least one implant part, wherein for forming the implant part a base member is produced from an implant material and this has a surface which is designed at least in the form of an artificial joint surface, wherein a wear-reducing hard material coating is applied to the entire or a part of the joint surface.

Various implants of the type described at the outset and methods for their production are known. Implants of this type are used, for example, in the form of hip and knee joint endoprostheses. A further field of use is vertebral prosthetics and, in this respect, in particular, vertebral disk prosthetics. Regardless of their end use, implants of the type described at the outset have a joint surface which is preferably designed to be wear-reducing. For this purpose, it is known to provide a base member, which forms an implant part, with a hard material coating, namely at least in an area of its surface which forms part of or the entire joint surface.

With known implants, there is normally, however, the problem that metal ions, for example, cobalt, chromium, molybdenum and/or nickel ions can leak from the implant material, namely through the hard material coating, as well. This leads to an increase in corrosion and also to an increase in the wear and tear on the implant, for example, due to flaking of the hard material coating. The negative effects described have the disadvantage that, as a result, the service life of the implant as well as the compatibility of the implant can be reduced; for example, the leakage of metal ions to a great extent from the implant material can cause allergic reactions.

Therefore, it would be desirable to provide an implant of the type described at the outset as well as a method for the production of an implant for extending the service life of the implant and for increasing the compatibility of the implant.

SUMMARY OF THE INVENTION

In accordance with the invention, an implant for insertion into a human or animal body comprises at least one implant part which has a base member produced from an implant material and a surface designed at least partially in the form of an artificial joint surface. Moreover, part of or the entire joint surface is covered by a wear-reducing hard material coating. Furthermore, an intermediate layer is provided between the hard material coating and the at least one joint surface formed from the implant material for the purpose of reducing tension between the hard material coating and the implant material.

BRIEF DESCRIPTION OF THE DRAWINGS

The foregoing summary and the following description may be better understood in conjunction with the drawing figures, of which:

FIG. 1: shows a side view of a femoral bone with an implanted condyle according to the invention;

FIG. 2: shows a view of the femoral bone from FIG. 1 in the direction of arrow A;

DETAILED DESCRIPTION OF PREFERRED EMBODIMENTS OF THE INVENTION

Figure 3:
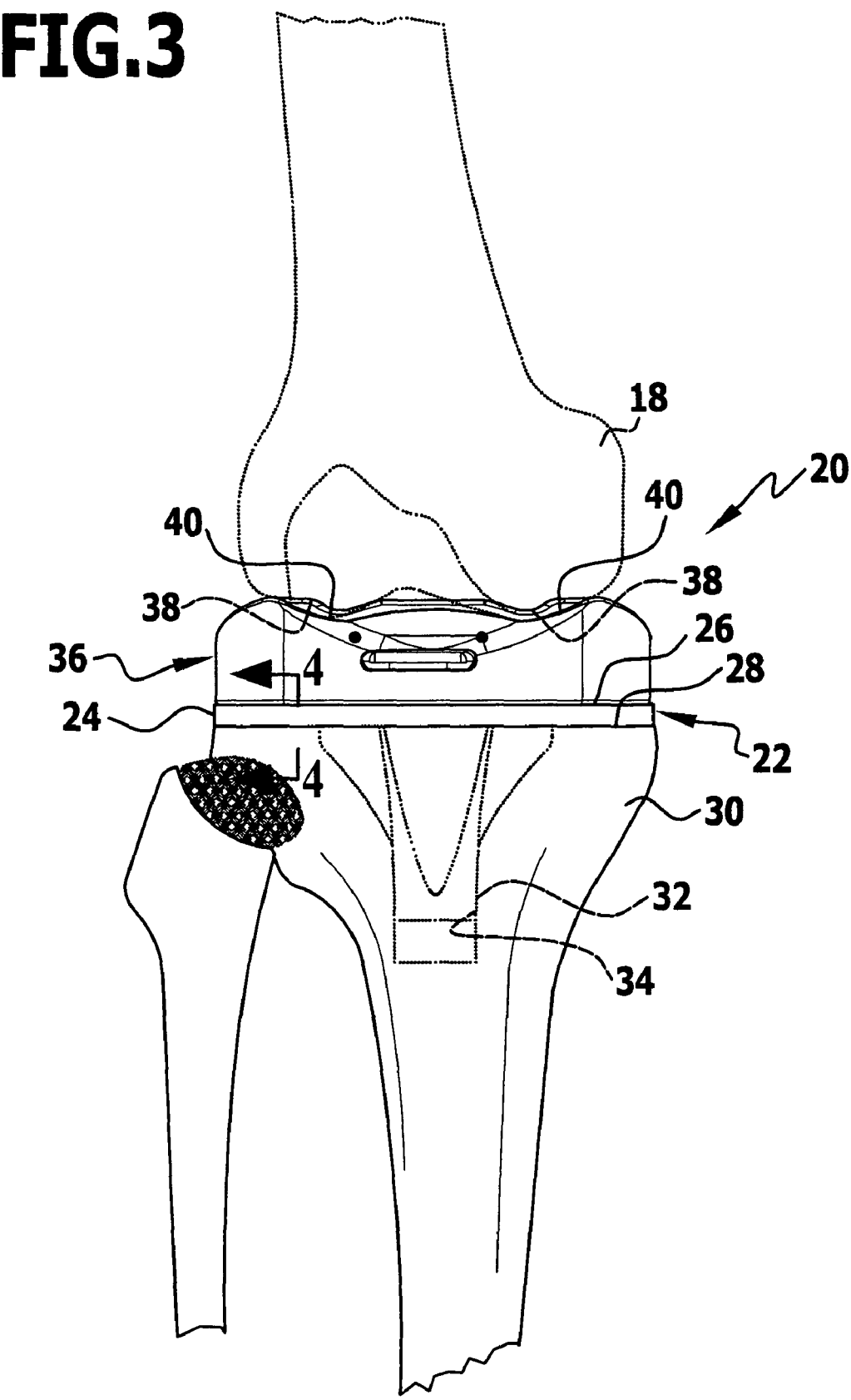
FIG. 3: shows a view of a partially artificial knee joint from the front.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to an implant for insertion into a human or animal body, said implant comprising at least one implant part, wherein the at least one implant part has a base member produced from an implant material and having a surface designed at least partially in the form of an artificial joint surface, wherein part of or the entire joint surface is covered by a wear-reducing hard material coating, wherein an intermediate layer is provided between the hard material coating and the at least one joint surface formed from the implant material for the purpose of reducing tension between the hard material coating and the implant material.

The intermediate layer suggested in accordance with the invention has, in particular, the property of reducing mechanical and/or electromechanical tension between the hard material coating and the implant material and/or inner tension in the hard material coating. This has the advantage that the hard material coating can be applied to the implant material in practice without any mechanical and/or electromechanical tension. As a result, it is made more difficult for metal ions, which would like to escape from the implant material, to pass to the outside not only through the intermediate layer but also through the hard material coating. As a result, corrosion of the implant material is decreased, on the one hand, and, on the other hand, wear and tear of the hard material coating is reduced. The intermediate layer can, in particular, also improve adherence of the hard material coating to the implant material. When the intermediate layer is, in particular, a layer low in defects, this forms condensation nuclei for an optimum overgrowth of the hard material coating.

The hard material coating is preferably designed in the form of a corrosion-inhibiting coating. Not only corrosion of the implant material following the implantation into a human or animal body but also corrosion of the hard material coating itself will be considerably reduced or even totally prevented as a result of such a hard material coating.

In order to prevent metal ions from being able to escape from the implant material and pass into the human or animal body, it is favorable when the hard material coating is designed in the form of a coating forming a metal ion barrier.

It is advantageous when the coating forming a metal ion barrier is a coating reducing the ion loss from the implant part by at least a factor of 10, preferably a coating reducing the ion loss by at least a factor of 20, in comparison with an implant part without any coating forming a metal ion barrier. With such a coating forming a metal ion barrier, the leakage of metal ions from the implant material can be reduced to at least one tenth in comparison with conventional implants.

The coating forming a metal ion barrier is favorably a barrier for cobalt, chromium, molybdenum and/or nickel ions. Such a coating forming a metal ion barrier is eminently suitable for conventional implant materials, for example, steels which contain cobalt, chromium, molybdenum and/or nickel.

The production of the hard material coating will be particularly simple and its hard wearing properties particularly high when the hard material coating comprises at least one ceramic layer.

The hard material coating is advantageously designed in the form of a multilayered layer system. As a result, properties of the hard material coating can be optimized individually. On the one hand, a necessary support effect for an outer covering layer can be improved and, on the other hand, any peeling of this covering layer can be effectively prevented. A multilayered layer system, which can be built up, for example, in the form of a "sandwich structure", improves, in addition, the fatigue resistance of the layer system itself. In addition, barriers for metal ions can be formed specifically as a result of several different layers.

In accordance with a preferred embodiment of the invention, it may be provided for the layer system to have an outer covering layer which points away from the implant part and at least one inner layer located beneath the covering layer and for a hardness of the covering layer to be greater than a hardness of the at least one inner layer. For example, the outer covering layer can be considerably harder than the at least one layer located beneath it which does, however, preferably have an adequate toughness for increasing a fatigue resistance of the layer system as well as preventing any peeling of the outer covering layer.

It is favorable when the covering layer contains zirconium (Zr) since layers or ceramics containing zirconium have a particularly great hardness and, therefore, a high abrasion resistance.

In order to improve the reduction in wear and tear on the hard material coating further, it is advantageous when the covering layer is zirconium nitride (ZrN). Apart from its great hardness, an altered wetting angle of the layer of zirconium nitride (ZrN) causes an improvement in the lubrication of the sliding surfaces and, therefore, contributes to an additional reduction in wear and tear.

Several inner layers are preferably formed. Several inner layers, preferably in the form of a "sandwich structure", increase a support effect for the covering layer and prevent its peeling to a high degree.

In order to increase hardness and the stability of the hard material coating, it is advantageous when the at least one inner layer is a nitride layer. Layers consisting of titanium nitride (TiN), titanium carbonitride (TiCN), chromium nitride (CrN) and chromium carbonitride (CrCn) are conceivable, in particular, as nitride layers.

The at least one inner layer preferably comprises at least one chromium nitride (CrN) layer. This hard layer increases a support effect of the layer system for the outer covering layer.

It is, in addition, favorable when the at least one inner layer comprises at least one chromium carbonitride (CrCN) layer. The chromium carbonitride (CrCN) layer containing carbon has great toughness which prevents, in particular, any peeling of additional layers, above all of the outer covering layer.

In order to be able to predetermine different properties of the layer system in a defined manner, it is favorable when at least two different inner layers are formed. Three, four or more different inner layers can also, of course, be provided.

In order to be able to form a highly efficient, inner layer system, it is advantageous when more than two inner layers are formed and when the at least two different inner layers are designed to be superimposed alternatingly. For example, an inner layer system consisting of inner layers of different hardness and toughness can be formed, for example, as a result of alternating layers of great hardness and great toughness.

Five inner layers are preferably formed. These can, in particular, comprise two different layers which are designed to be superimposed alternatingly, i.e., for example, in a sequence of layers A-B-A-B-A. One of the two layers can, in particular, be a chromium nitride (CrN) layer and the other of the two different layers a chromium carbonitride (CrCN) layer, wherein the outer layers of the layer system are preferably formed by chromium nitride (CRN) layers. Five inner layers are, on the one hand, easy to produce and, on the other hand, a very good adhesion of the outer covering layer as well as an efficient metal ion barrier can already be formed with five layers. Alternatively, titanium nitride (TiN) layers and titanium carbonitride (TiCN) layers can also be provided as different layers.

In order to ensure a particularly good adhesion of the outer covering layer to the at least one inner layer, it is advantageous when the covering layer directly covers an inner layer consisting of chromium nitride (CrN). An excellent stability of the hard material coating can be achieved, in particular, when the outer covering layer is also a nitride layer.

The intermediate layer is advantageously a metallic layer. A metallic layer may be applied to a metallic implant material particularly easily. In addition, a metallic intermediate layer adheres particularly well to a metallic implant material.

The intermediate layer preferably contains no metal which is contained in the implant material. Such an intermediate layer forms an additional barrier for metal ions escaping from the implant material.

In accordance with a preferred embodiment of the invention, it may be provided for the intermediate layer to be a layer consisting of a zirconium alloy, of a niobium alloy, of a tantalum alloy, of pure niobium, of pure tantalum or of pure zirconium. A pure zirconium layer, which is advantageously applied by way of physical vapor deposition (PVD), is, in particular, especially low in defects and so mechanical tensions which would occur if the hard material coating were to be applied directly onto the implant material are considerably reduced. A layer consisting of pure zirconium has, in addition, the advantage that it is more or less defect-free, i.e., also has no so-called "pin holes", through which charges and, in particular, also ions from the implant material can pass into the hard material coating or pass through it.

A particularly good adhesion of the hard material coating and/or the intermediate layer is achieved when the hard material coating and/or the intermediate layer are layers applied by way of physical vapor deposition (PVD). Several layers can, in particular, be specifically applied one after the other as a result.

The intermediate layer advantageously has a thickness in a range of $30 \times 10^{-9}$ m to $200 \times 10^{-9}$ m. The thickness of the layer is preferably 50 to 100 nm. A layer consisting of metallic zirconium has, in particular, excellent adhesive properties and, in addition, seals the implant material, whereby any leakage of metal ions from the implant material can be reduced.

In order to increase the service life of the implant, it is advantageous when the hard material coating has a scratch resistance of at least 100 N. Wear and tear on the hard material coating may be minimized in this way.

The implant material preferably contains cobalt or is a cobalt alloy. It is, therefore, possible to use conventional implant materials for the production of an implant according to the invention.

It is advantageous when the cobalt alloy is a cobalt-chromium-molybdenum alloy. In this respect, it is preferably a CoCr29Mo6 alloy.

In accordance with one preferred embodiment of the invention, it may be provided for the implant to be an artificial hip or knee joint, a vertebral body replacement implant or an artificial intervertebral disk prosthesis.

The at least one implant part is preferably a joint ball or a joint socket of a hip joint prosthesis, an artificial condyle or a tibial plate of a knee joint prosthesis or a contact element of an intervertebral disk prosthesis having or bearing a joint surface.

The object specified at the outset is accomplished in accordance with the invention, in addition, by a method of the type described at the outset in that prior to the application of the hard material coating an intermediate layer is applied to the at least one part of the joint surface for the purpose of reducing mechanical tension between the hard material coating and the implant material.

As already mentioned above, the leakage of metal ions from the implant material is considerably decreased by the intermediate layer and, in addition, the adherence of the hard material coating to the implant material also improved. As a result, the risk of corrosion of the implant can be reduced and the service life of the implant increased. In addition, implants can also be produced for people with allergies from materials which would not be suitable for the production of implants for people with allergies on account of materials which would otherwise normally leak and cause an allergic reaction. The desired properties of the hard material coating can be considerably improved, in particular, by an intermediate layer which is low in defects.

So that layers of a more or less optional type and thickness can be applied to the implant part, it is favorable when the hard material coating and/or the intermediate layer are applied by way of physical vapor deposition (PVD).

In order to achieve an optimum connection between the hard material coating and the implant material, it is advantageous when the intermediate layer is applied with a thickness in a range of $30 \times 10^{-9}$ m to $200 \times 10^{-9}$ m. The intermediate layer is preferably applied with a thickness in the range of 50 to 100 nm. An intermediate layer with a thickness in the specified range is sufficient to seal the implant material, in particular, when the intermediate layer is very low in defects, such as, for example, an intermediate layer consisting of pure zirconium.

A metallic layer is advantageously applied as intermediate layer. A layer consisting of pure zirconium is, in particular, eminently suitable for sealing the implant material and achieving an optimum connection between the hard material coating and the implant material.

In order to form as good a layer as possible forming a barrier for metal ions, it is favorable when a layer is applied as intermediate layer which contains no metal which is contained in the implant material.

A layer consisting of a zirconium alloy, a ceramic containing zirconium or of pure zirconium is preferably applied as intermediate layer. Intermediate layers of this type are particularly suitable for sealing the implant material completely.

Furthermore, the object specified at the outset is accomplished by the use of one of the methods described above for the production of an implant in the form of an artificial hip or knee joint, a vertebral body replacement implant or an artificial intervertebral disk prosthesis.

The following description of preferred embodiments of the invention serves to explain the invention in greater detail in conjunction with the drawings.

Implants according to the invention can be designed, for example, in the form of knee joint prostheses, hip joint prostheses or intervertebral disk prostheses. This list is not, however, final.

In the case of a knee joint prosthesis, it is conceivable to design a part of the knee joint prosthesis which can be connected to a femur 18 in the form of an implant part according to the present invention, for example, in the form of an implant part 10 which is illustrated by way of example in FIGS. 1 and 2 in the form of an artificial condyle. The implant part 10 has an articulation surface which forms a joint surface 12. A bone contact surface 14 of the implant part 10, which points in the opposite direction, abuts on a prepared bone surface 16 of the femur 18.

In addition, a further implant part according to the invention can be provided for forming an implant 20 in the form of a knee joint prosthesis and this is provided in FIG. 3 with the reference numeral 22 and designed in the form of a tibial part. The implant part 22 comprises a tibial plate 24 with a flat joint surface 26 which abuts on a prepared, flat bone surface 28 of a tibia 30. The implant part 22 has, in addition, a shaft 32 which is anchored in a recess 34 in the tibia prepared for this purpose.

The implant part 20 can, in addition, comprise a meniscus part 36 which is mounted on the implant part 22 so as to be movable. The meniscus part 36 has two articulation surfaces 40 which correspond to condyles 38 of the femur. The articulation surfaces 40 can, in particular, be designed to correspond to the joint surface 12 of the implant part 10.

Figure 4:
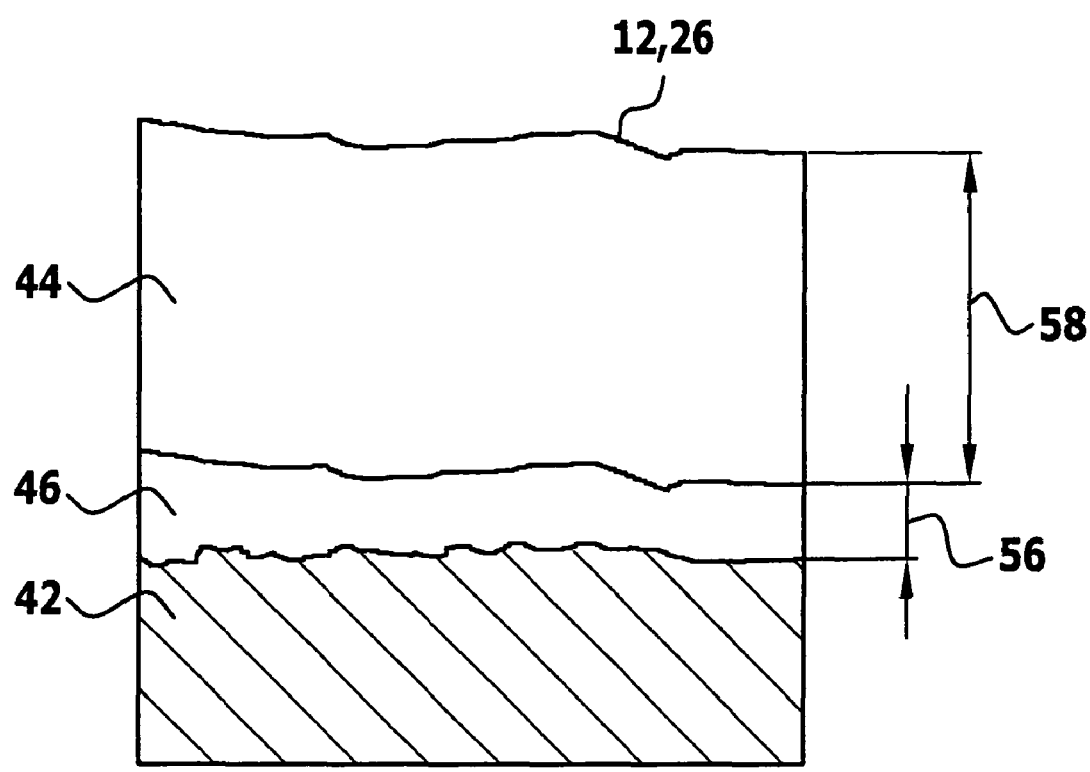
FIG. 4: shows a side view along line 4-4 in FIGS. 1 and 3.
Figure 5:
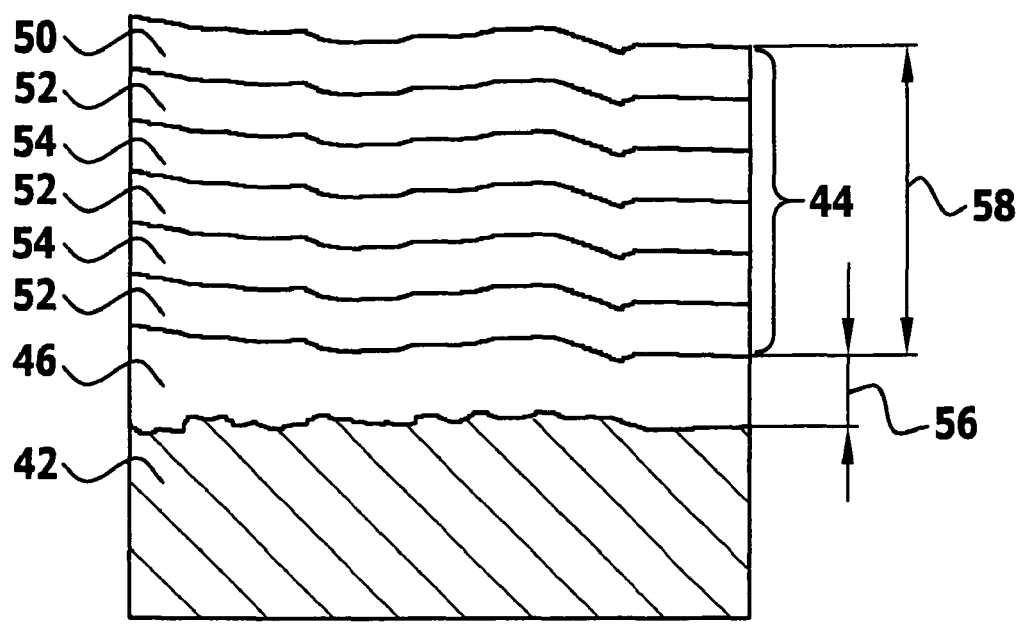
FIG. 5: shows a view analogous to FIG. 4 with a multilayered hard material coating system.

The joint surface 12 of the implant part 10 and the joint surface 26 of the implant part 22 are provided at least partially, preferably completely, with a hard material coating. A base member 42 of the implant parts 10 and 22, which is preferably produced from an implant steel, for example, a cobalt-chromium-molybdenum alloy, such as, for example, CoCr29Mo6, is provided with a hard material coating 44, as illustrated by way of example in FIGS. 4 and 5.

An intermediate layer 46, which reduces mechanical tension between the hard material coating 44 and the implant material, from which the base member 42 is formed, is applied between the base member 42 and the hard material coating 44.

The hard material coating 44 may have a thickness in a range of $50 \times 10^{-6}$ m to $500 \times 10^{-6}$ m. The hard material coating 44 can be applied in the form of a single layer or also, however, in the form of a layer system 48 which is built up from two or more layers. A layer system 48 consisting of several layers comprises, in particular, an outer covering layer 50 which is preferably designed in the form of a wear-resistant zirconium nitride layer (ZrN). It preferably has a thickness in a range of $1\times10^{-6}$ m to $10\times10^{-6}$ m.

One or more inner layers of the layer system 48 can be provided beneath the covering layer 50. The inner layers are preferably designed in the form of tough and hard layers 52 and 54, respectively, which can form the layer system 48, in particular, by being superimposed alternatingly. A chromium nitride (CrN) layer is mentioned as one example for a hard, inner layer 52; layers consisting of chromium carbonitride (CrCN) are particularly suitable as tough layers 54.

Particularly good properties of the hard material coating 44 are achieved when hard and tough layers are provided alternatingly. They give the outer covering layer the necessary support effect and prevent its peeling to a high degree. Furthermore, the resistance to fatigue of the layer system is decisively and positively influenced by such a "sandwich structure". The covering layer, for example, a zirconium nitride (ZrN) covering layer is adjusted in its hardness to the hardness of the hard layers 52 and essentially takes over the wear-reducing function of the hard material coating 44. Apart from its considerable hardness, it has surprisingly been shown in the case of a zirconium nitride (ZrN) covering layer that with this layer, in particular, an altered wetting angle causes an improvement in the lubrication of the joint surface 12 and the joint surface 26, respectively, and, as a result, contributes to a reduction in wear and tear.

The intermediate layer 46, which is preferably formed from pure zirconium, is practically free from defects, i.e., no so-called "pin holes" are formed which make it possible to transport a charge, in particular, also in the form of metal ions from the base member 42 to the outside.

The hard material coating 44, in particular, when it is designed in the form of a layer system 48, not only has a positive effect on the stability but also prevents any loss of metal ions from the base member 42. Any leakage of metal ions from an implant part 10 and 22, respectively, can lead to allergic reactions in some patients and is not, in any way, desirable. The layer system 48 as suggested makes it possible, in particular, to reduce any ion loss of cobalt, chromium, molybdenum and/or nickel from the implant material of the base member 42 by at least 20 times in comparison with conventional implants. The ion loss is reduced, in addition, by the preferably defect-free intermediate layer 46. It is of particular advantage when the intermediate layer 46 is formed from a metal which is not contained in the implant material, from which the base member 42 is produced.

The hard material coating 44 or the individual layers thereof are preferably applied by means of physical vapor deposition and therefore form so-called "PVD layers" (physical vapor deposition). The layers could, alternatively, also be applied by way of cold gas spray coating. The intermediate layer preferably has a thickness in a range of $50\times10^{-9}$ m to $100\times10^{-9}$ m, the hard material coating 44 an overall thickness 58 in a range of $1\times10^{-6}$ m to $10\times10^{-6}$ m. Thicknesses of the individual layers of the layer system 48, in particular, the hard layer 52 and the tough layer 54 are in a range of $200\times10^{-9}$ m to $1000\times10^{-9}$ m. The covering layer 50 preferably has a thickness in a range of $1\times10^{-6}$ m to $5\times10^{-6}$ m.

It is possible, in particular, due to the multilayered layer system 48 to adapt the known, good wear protection properties of hard material layers for the tribological, corrosive and dynamic stress profile in the case of joint prostheses, in particular, in the case of knee joint endoprostheses. The individual layers have a barrier function and, at the same time, a high adhesive strength and an excellent resistance to fatigue as a result of the hardness gradient of the layers and the graded distribution of compressive stress in the individual layers. A graduation, in particular, of the carbon within the tough layers 54, for example, within chromium carbonitride (CrCN) layers has shown that a distribution of residual compressive stress can be built up in this way such that a scratch resistance of the hard material coating 44 is, altogether, over 100 N. Typical, known PVD layers have a scratch resistance only in a range of between 50 N and 70 N.

What is claimed is:

1. Implant for insertion into a human or animal body, comprising:
   at least one implant part having a base member produced from an implant material and having a surface designed at least partially in a form of an artificial joint surface,
   a wear-reducing hard material coating covering at least part of the joint surface,
   an intermediate layer provided between the hard material coating and the joint surface for the purpose of reducing tension between the hard material coating and the implant material,
   wherein:
   the hard material coating is designed as a multilayered layer system;
   the layer system has an outer covering layer pointing away from the implant part and at least one inner layer located beneath the covering layer;
   a hardness of the covering layer is greater than a hardness of the at least one inner layer;
   the at least one inner layer comprises at least one of a chromium nitride (CrN) layer and a chromium carbonitride (CrCN) layer; and
   the covering layer either contains zirconium (Zr) or is zirconium nitride (ZrN).

2. Implant as defined in claim 1, wherein the hard material coating is designed as a corrosion-inhibiting coating.

3. Implant as defined in claim 1, wherein the hard material coating is designed as a coating forming a metal ion barrier.

4. Implant as defined in claim 3, wherein the coating forming a metal ion barrier is a coating reducing ion loss from the implant part by at least a factor of 10 in comparison with an implant part without any coating forming a metal ion barrier.

5. Implant as defined in claim 3, wherein the coating forming a metal ion barrier is a coating forming a barrier for at least one of cobalt, chromium, molybdenum and nickel ions.

6. Implant as defined in claim 1, wherein the hard material coating comprises at least one ceramic layer.

7. Implant as defined in claim 1, wherein several inner layers are formed.

8. Implant as defined in claim 7, wherein at least two different inner layers are formed.

9. Implant as defined in claim 8, wherein more than two inner layers are formed and wherein the at least two different inner layers are designed to be superimposed alternatingly.

10. Implant as defined in claim 7, wherein five inner layers are formed.

11. Implant as defined in claim 1, wherein the covering layer directly covers an inner layer consisting of chromium nitride (CrN).

12. Implant as defined in claim 1, wherein the intermediate layer is a metallic layer.

13. Implant as defined in claim 12, wherein the intermediate layer contains no metal contained in the implant material.

14. Implant as defined in claim 1, wherein the intermediate layer is a layer consisting of a zirconium alloy, of a niobium alloy, of a tantalum alloy, of pure niobium, of pure tantalum or of pure zirconium.

15. Implant as defined in claim 1, wherein at least one of the hard material coating and the intermediate layer are layers applied by way of physical vapor deposition.

16. Implant as defined in claim 1, wherein the intermediate layer has a thickness in a range of $30 \times 10^{-9}$ m to $200 \times 10^{-9}$ m.

17. Implant as defined in claim 1, wherein the hard material coating has a thickness in a range of $50 \times 10^{-6}$ m to $500 \times 10^{-6}$ m.

18. Implant as defined in claim 1, wherein the hard material coating has a scratch resistance of at least 100 N.

19. Implant as defined in claim 1, wherein the implant material contains cobalt or is a cobalt alloy.

20. Implant as defined in claim 19, wherein the cobalt alloy is a cobalt-chromium-molybdenum alloy (CoCr29Mo6).

21. Implant as defined in claim 1, wherein the implant is an artificial hip or knee joint, a vertebral body replacement implant or an artificial intervertebral disk prosthesis.

22. Implant as defined in claim 1, wherein the at least one implant part is a joint ball or a joint socket of a hip joint prosthesis, an artificial condyle or a tibial plate of a knee joint prosthesis or a contact element of an intervertebral disk prosthesis having or bearing a joint surface.

23. Method for the production of an implant for insertion into a human or animal body, said implant comprising at least one implant part, the method comprising:
    producing a base member of the at least one implant part from an implant material, the base member having a surface designed at least partially in a form of an artificial joint surface,
    applying a wear-reducing hard material coating to at least part of the joint surface,
    prior to the application of the hard material coating, applying an intermediate layer to at least part of the joint surface for the purpose of reducing mechanical tension between the hard material coating and the implant material,
    wherein:
        the hard material coating is designed as a multilayered layer system;
        the layer system has an outer covering layer pointing away from the implant part and at least one inner layer located beneath the covering layer;
        a hardness of the covering layer is greater than a hardness of the at least one inner layer;
        the at least one inner layer comprises at least one of a chromium nitride (CrN) layer and a chromium carbonitride (CrCN) layer; and
        the covering layer either contains zirconium (Zr) or is zirconium nitride (ZrN).

24. Method as defined in claim 23, wherein at least one of the hard material coating and the intermediate layer are applied by way of physical vapor deposition.

25. Method as defined in claim 23, wherein the intermediate layer is applied with a thickness in a range of $30 \times 10^{-9}$ m to $200 \times 10^{-9}$ m.

26. Method as defined in claim 23, wherein a metallic layer is applied as an intermediate layer.

27. Method as defined in claim 23, wherein a layer containing no metal contained in the implant material is applied as an intermediate layer.

28. Method as defined in claim 23, wherein a layer consisting of a zirconium alloy, a ceramic containing zirconium or of pure zirconium is applied as an intermediate layer.

29. Method as defined in claim 23, wherein the implant is produced in a form of an artificial hip or knee joint, a vertebral body replacement implant or an artificial intervertebral disk prosthesis.

* * * * *